United States Patent [19]

Fosslien

[11] 4,130,754
[45] Dec. 19, 1978

[54] PARTICLE COUNTING
[75] Inventor: Egil Fosslien, Tampa, Fla.
[73] Assignee: Cortex Research Corporation, Tampa, Fla.
[21] Appl. No.: 807,251
[22] Filed: Jun. 16, 1977
[51] Int. Cl.[2] .................... G06M 11/00; G01N 27/10
[52] U.S. Cl. ........................... 235/92 PC; 235/92 CP; 235/92 R; 324/71 CP
[58] Field of Search ........ 235/92 PC, 92 DM, 92 CP, 235/92 PL; 324/71 CP, 30 R; 364/555

[56] References Cited
U.S. PATENT DOCUMENTS

| | | | |
|---|---|---|---|
| 2,656,508 | 10/1953 | Coulter | 324/71 CP |
| 2,869,078 | 1/1959 | Coulter et al. | 324/71 CP |
| 3,015,775 | 1/1962 | Coulter et al. | 324/71 CP |
| 3,273,402 | 9/1966 | Farr | 73/425.6 |
| 3,657,725 | 4/1970 | Estelle et al. | 235/92 PC |
| 3,769,582 | 10/1973 | Schoen | 324/71 CP |
| 3,781,675 | 12/1973 | Angel | 324/71 CP |
| 3,846,701 | 11/1974 | Sampey | 235/92 DM |
| 3,865,305 | 2/1975 | Sampey | 235/92 DM |
| 3,874,850 | 4/1975 | Sorensen et al. | 324/30 R |
| 3,921,066 | 11/1975 | Angel et al. | 324/71 CP |

Primary Examiner—Joseph M. Thesz
Attorney, Agent, or Firm—Koenig, Senniger, Powers and Leavitt

[57] ABSTRACT

Apparatus for counting particles, such as blood cells, suspended in a liquid medium. A chamber receives a sample of the liquid medium containing particles and the sample flows from the chamber through a conduit. The conduit is normally closed but is opened for flow of the sample therethrough with the sample being drawn through the conduit upon its being opened. A counter counts particles in the sample as it flows through the conduit and a single manual operation opens the conduit for flow of a sample therethrough and concomitantly actuates the counter to count the particles in the sample flowing through the conduit. A method of counting particles suspended in a liquid medium is also disclosed.

49 Claims, 10 Drawing Figures

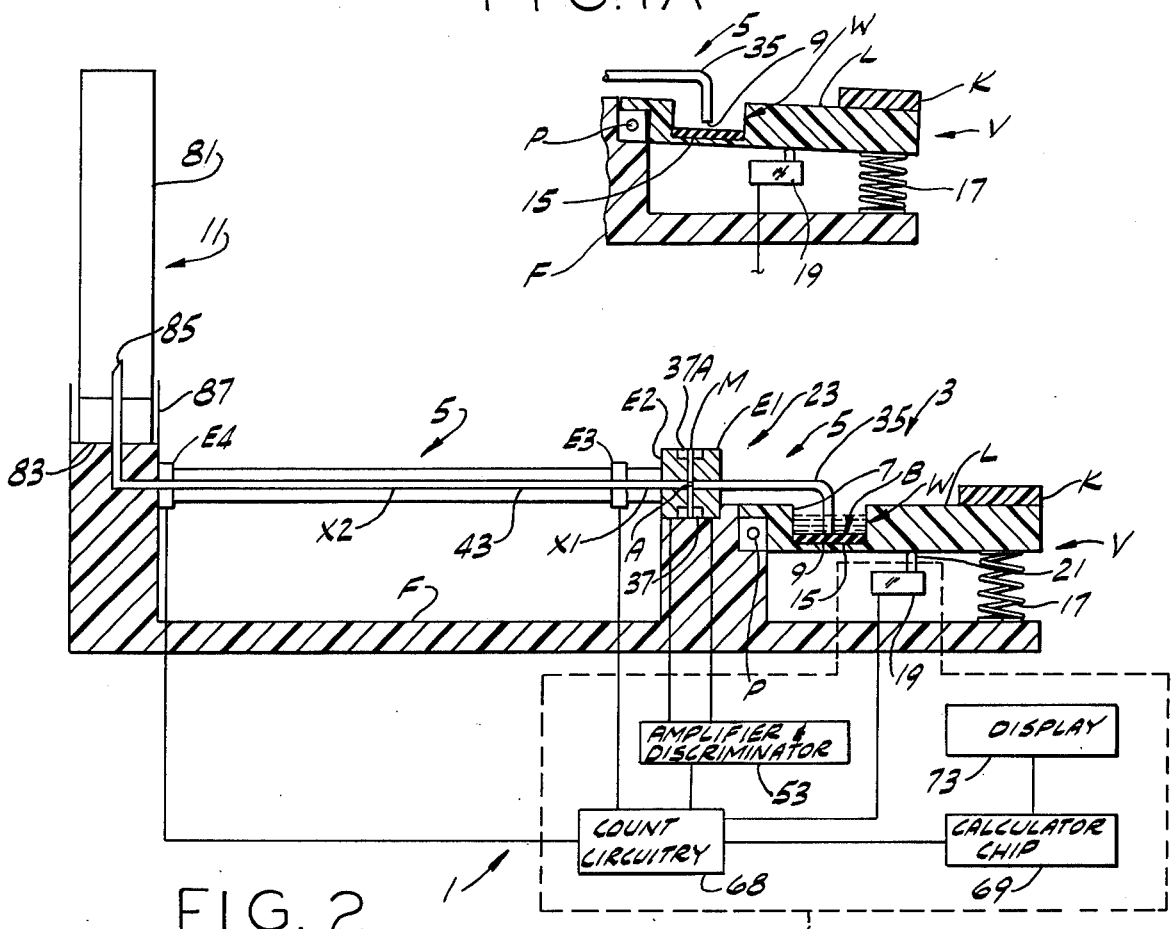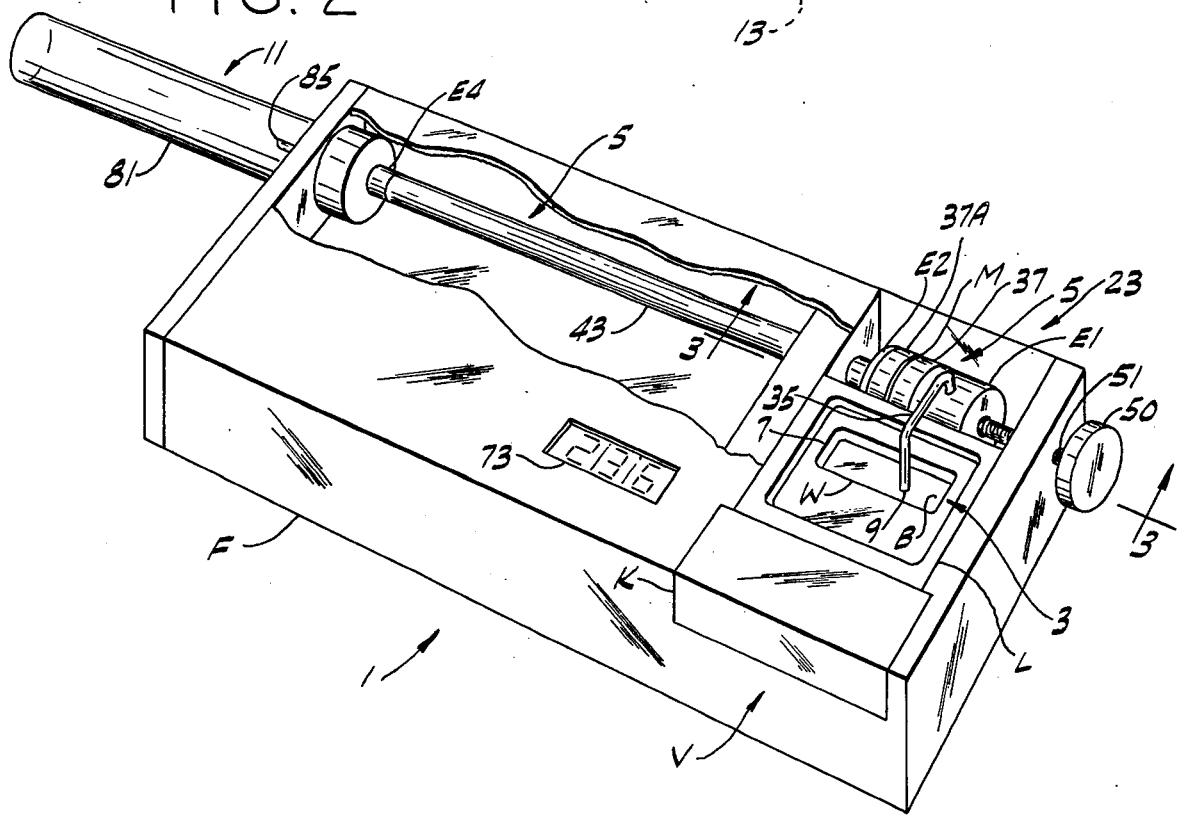

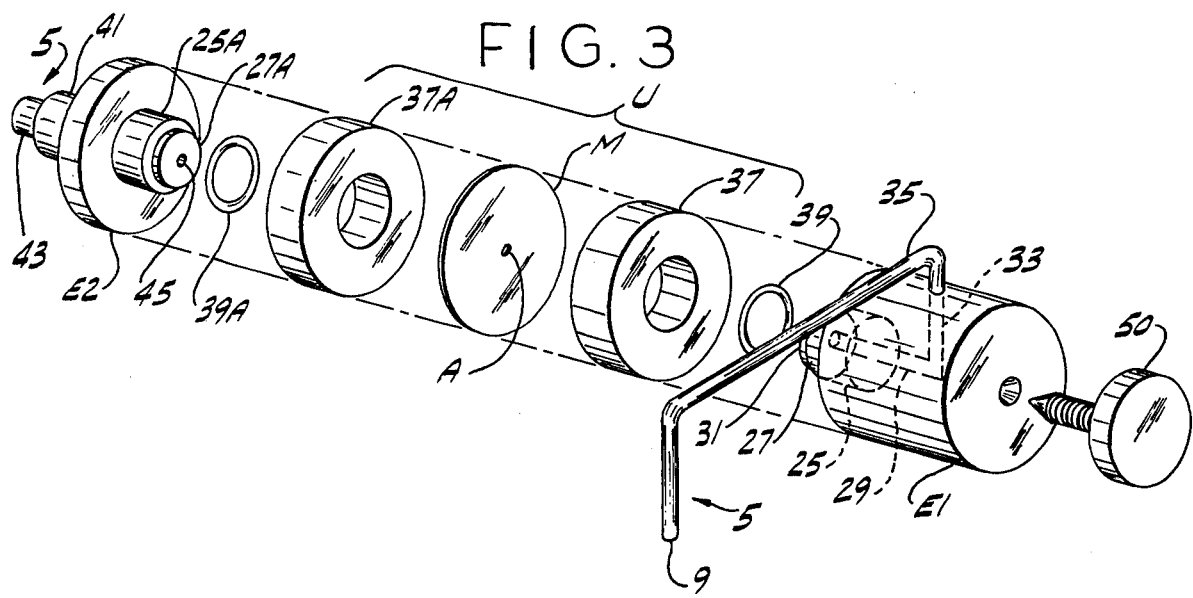
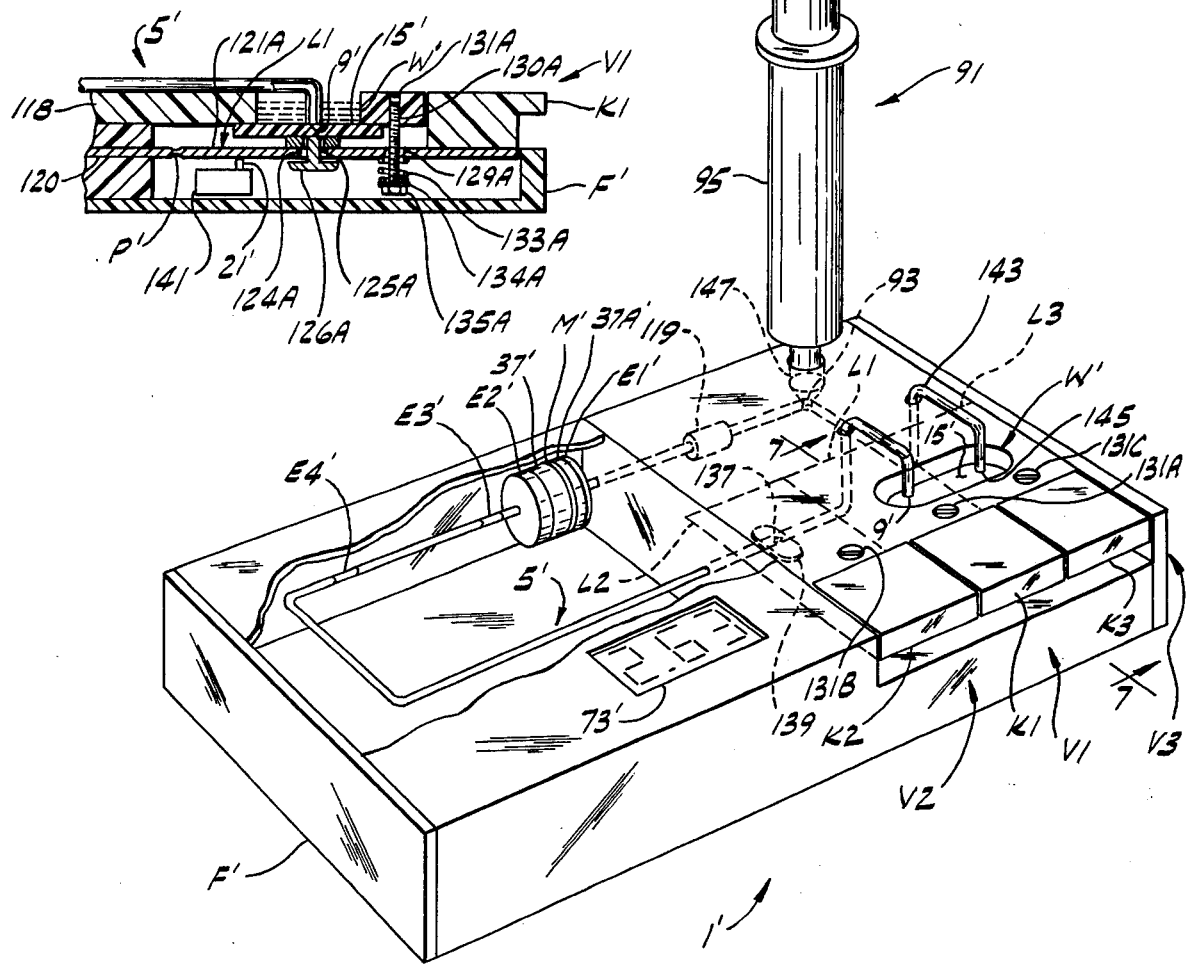

PARTICLE COUNTING

BACKGROUND OF THE INVENTION

This invention relates to particle counting apparatus and more particularly to apparatus and a method for counting particles such as blood cells suspended in a liquid medium.

In the medical field, particle counters are used, for example, to count white blood cells in a sample of a patient's blood with the resultant count value used in making a diagnosis. Many techniques have been employed in particle counting, among these being colorimetry, microscope counting using a chamber, light scattering from particles in non-coaxial or coaxial (sheath) flow and aperture conductivity counting. Representative patents in which this latter technique is disclosed are U.S. Pat. Nos. 2,656,508 and 2,869,078. In addition, some particle counters using aperture conductivity counting also introduce air bubbles into the flow stream of a sample to separate the sample into two or more portions and the volume of these portions, for which a particle count is made, is metered by use of electro-optical gating circuits. A representative patent in which this technique is disclosed is U.S. Pat. No. 3,657,725.

These previously developed counters all require pumps, solenoids or motors and are quite costly, bulky in size and must be supplied with power from typical utility sources. Additionally, the test procedures which must be followed in using one of these counters to obtain accurate results are typically involved and complex. Thus, such counters are usually found only in a hospital or a laboratory. This complicates and unduly lengthens a physician's task of diagnosing a patient's illness when he thinks a cell count should be made for a sample of the patient's blood because he must take a blood sample from the patient, tag it, send it to a laboratory for testing and then await the test results before prescribing a course of treatment for the patient.

SUMMARY OF THE INVENTION

Among the several objects of the present invention may be noted the provision of apparatus for counting particles, such as blood cells, suspended in a liquid medium without the need of a complicated test setup or external power; the provision of such apparatus which is simple to operate and in which a particle count is initiated by a single manual operation; the provision of such apparatus with which multiple particle counts may be obtained from a single sample of, for example, a patient's blood; the provision of such apparatus which is readily calibrated to obtain consistently accurate data when one or more counts are performed; the provision of such apparatus for performing a particle count for a predetermined volume of a sample; the provision of such apparatus for providing a particle count in standard units of measurement so that no conversion is required to obtain useful data; the provision of such apparatus in which waste fluids are readily accumulated and easily disposed of; the provision of such apparatus having a reusable motive power source; the provision of such apparatus which may be readily cleaned to prevent clogging and contamination; the provision of such apparatus whose components which are most likely to become clogged are easily replaceable; the provision of such apparatus which is lightweight, compact, portable and self-contained so that it may, for example, be used in the field on expeditions or during military maneuvers or by a doctor at his office and then transported by him in his medical kit to a patient's home for use there; and the provision of such apparatus which is inexpensive and yet sturdy in construction and reliable in operation.

Briefly, apparatus of the present invention for counting particles, such as blood cells, suspended in a liquid medium, comprises a chamber for receiving a sample of the liquid medium containing particles and a conduit for flow of the sample from the chamber. Means normally closing the conduit are opened for flow of the sample therethrough and means are provided for drawing the sample through the conduit upon opening of the conduit-closing means. Counting means count particles in the sample as it flows through the conduit and manually operable means open the conduit-closing means for flow of a sample therethrough and concomitantly actuate the counting means to count the particles in the sample flowing through the conduit.

The invention also includes a method for counting particles, such as blood cells, suspended in a liquid medium by placing in a chamber a first sample of a liquid medium having a known quantity of particles in a predetermined volume thereof. The first sample is then drawn from the chamber through a conduit and the particles in the first sample are counted as it flows through the conduit. The number of particles counted in the first sample are divided by a number equal to the known quantity thereby to produce a calibration factor. A second sample of a liquid medium having an unknown quantity of particles therein is placed in the chamber and drawn through the conduit and particles in the second sample are counted as it flows through the conduit. The number of particles counted in the second sample are divided by the calibration factor to produce a number representative of the actual particle count for the second sample. Other objects and features will be in part apparent and in part pointed out hereinafter.

BRIEF DESCRIPTION OF THE DRAWINGS

FIG. 1 is a schematic representation and block diagram of particle counting apparatus of the present invention;

FIG. 1A illustrates the moved position of a portion of the apparatus of FIG. 1;

FIG. 2 is a perspective view with parts broken away of a first embodiment of the particle counting apparatus of the invention;

FIG. 3 is an exploded enlarged view taken along line 3—3 in FIG. 2 of an assembly through which a sample of a liquid medium flows and within which particles in the sample are sensed;

FIG. 6 is a perspective view with parts broken away of a second embodiment of particle counting apparatus of the invention;

FIG. 7 is a sectional view of the particle counting apparatus shown in FIG. 6 taken along line 7—7;

Corresponding reference characters indicate corresponding parts throughout the several views of the drawings.

DESCRIPTION OF PREFERRED EMBODIMENTS

Figure 4:
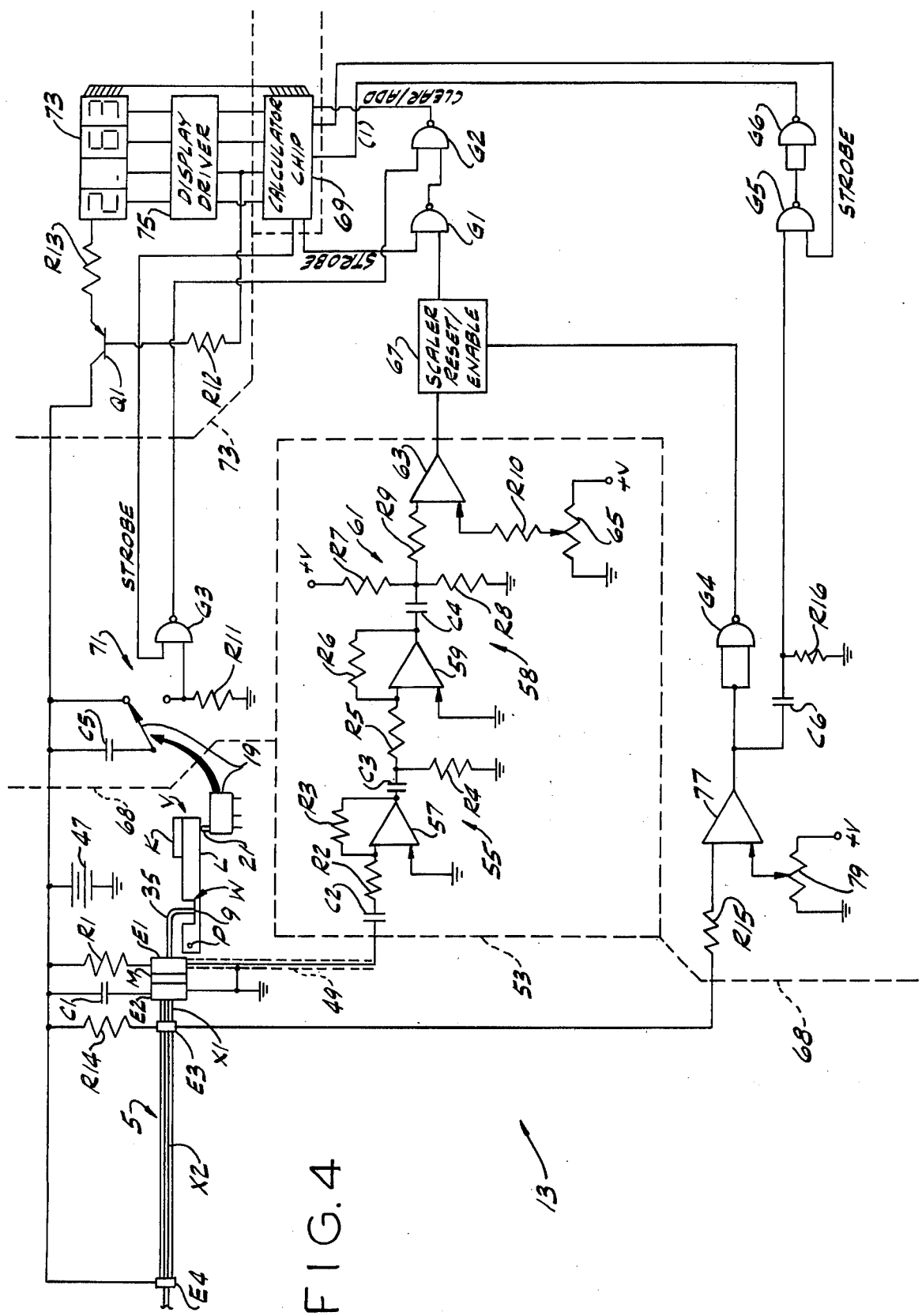
FIG. 4 is a schematic circuit diagram of a first embodiment of particle counting circuitry of the apparatus.

Referring now to the drawings, apparatus of the present invention for counting particles, such as blood cells, suspended in a liquid medium is indicated in its entirety at 1 and comprises a chamber generally indicated 3 for receiving a sample of the liquid medium. The sample flows from chamber 3 through a conduit generally indicated 5 which is normally closed but which is opened for flow of the sample therethrough. As shown in FIGS. 1 and 2, chamber 3 is in the form of a well W which is open at the top for receiving a sample and which has a bottom B and sides 7. The well is formed in a block of synthetic resin or other suitable material. Conduit 5 has an inlet end 9 extending down into well W towards its bottom. The bottom of the well and the inlet end of the conduit are relatively movable between a closed position in which the bottom closes the inlet end of the conduit and an open position in which the bottom and the inlet end are spaced apart for entry of the sample into the conduit. For this purpose, the inlet end of the conduit is fixed and the bottom of the well is flexible and flexes from the conduit closed position in which the bottom engages the inlet end of the conduit to the conduit open position. A source of negative pressure 11 draws sample through conduit 5 upon opening of the inlet end of the conduit and particles in the sample are counted by particle counting and display circuitry 13 as the sample flows through the conduit. A valve, generally indicated V, is manually operable to open closed conduit 5 for flow of a sample therethrough and manual operation of the valve concomitantly actuates counting circuitry 13 to count the particles in the sample flowing through the conduit.

The bottom of well W is a flexible diaphragm 15 which is a suitable elastomer material such as rubber and manual operation of valve V involves flexing of the diaphragm. As best shown in FIGS. 1 and 4, valve V includes a lever L for moving the diaphragm away from the inlet end of the conduit. The lever is movable about a pivot P which is located at one end of the lever. At the other end of the lever (its free end) is a key K for moving the lever about its pivot when manual force is applied to the key. A spring 17 is seated against the inside surface of the bottom of a frame F in which particle counter 1 is housed and the spring biases the lever and the diaphragm toward the conduit closing position. Movement of the lever about its pivot when manual force is applied to the key moves the diaphragm downwardly and away from the inlet end of the conduit. This opens the inlet end of the conduit and sample in well W may then be drawn off into the conduit. Counting circuitry 13 includes a reset switch 19 actuable by lever L as it simultaneously moves the diaphragm away from the conduit closing position. As shown, switch 19 is a microswitch positioned beneath lever L and the switch has an actuator 21 which is contacted and depressed by the lever as it rotates about its pivot thereby closing the switch. The switch is opened when the plunger returns to its normal position upon release of the lever. Actuation of switch 19 resets the counting circuitry to enable it to count particles in the next sample subsequently flowing through the conduit.

The counting circuitry includes a particle detector generally indicated 23 which detects particles in the sample and produces an electrical signal indicative of the particles detected. For this purpose, the medium in which particles are suspended is electrically conductive and an electrical circuit path is completed through the sample as it flows through the conduit. The conductivity of this path is varied by particles in the sample to produce the electrical signal. Referring to FIGS. 2–4, particle detector 23 includes a pair of electrodes E1 and E2 positioned downstream from the inlet end of conduit 5. As shown in FIG. 3, electrode E1 is of tubular cylindrical form and has first and second reduced diameter extensions 25 and 27 respectively, the diameter of the second being smaller than that of the first. The electrode has a longitudinal central bore 29 extending inwardly from end 31 of section 27 partially through the main body of the electrode. A radial bore 33 extends from the inward end of bore 29 to the outer surface of the electrode. A tube portion 35 of conduit 5 has one end which constitutes the inlet end of the conduit and the other end of the tube portion is received in the radial bore of the electrode. A centering ring 37 is sized to fit over extension 25 of the electrode and an O-ring 39 is sized to fit over extension 27 of the electrode. The centering ring is made of a suitable electrically non-conductive material such as a synthetic resin material sold under the trademark Lucite by E. I. duPont de Nemours & Co.

The other electrode is also of tubular cylindrical form and has first and second reduced diameter extensions 25A and 27A respectively with the diameter of the second being smaller than that of the first. These extensions correspond in size and shape to those of electrode E1 and a centering ring 37A and an O-ring 39A fit over these extensions in the same manner that centering ring 37 and O-ring 39 fit over the corresponding extensions of electrode E1. Electrode E2 has a third reduced diameter extension 41 which is on the opposite side of the main body of the electrode from the other two reduced diameter extensions and a tube portion 43 of conduit 5 mates with extension 41. The electrode has a longitudinal central bore 45 so a sample entering inlet end 9 of conduit 5 flows through tube portion 35 of the conduit, electrode E1, electrode E2 and through tube portion 43 to negative pressure source 11. A battery 47 has one terminal connected to electrode E1 through a resistor R1 and to electrode E2 through a capacitor C1. Electrode E1 is further connected to the counting portion of the particle counter circuitry through a shielded conductor 49 while electrode E2 and the shield of the conductor are grounded. An electrical circuit path is thus completed between the electrodes through the sample when the sample is simultaneously flowing through both electrodes.

A disk-shaped electrically non-conductive member constituted by a membrane M is positioned between electrodes E1 and E2 and is aligned with respect to the fluid flow path through conduit 5 by centering rings 37 and 37A. Membrane M, formed for example of a plastic film material such as that sold under the trademark Mylar, has an aperture A sized to require particles in the sample to individually pass through the aperture. The size of the aperture is, for example, 100 microns. Because the membrane is non-conductive, the conductivity of the circuit path between the electrodes varies as a function of the degree of blockage of aperture A which occurs when a particle passes through the aperture.

Thus each particle in the sample momentarily affects the conductivity of the circuit path between the electrodes and a resulting signal element of the electrical signal is produced at electrode E1 and transmitted via shielded conductor 49 to the input of the counting circuitry. A clamping and retaining screw 50 is threaded through a threaded hole 51 in the side of frame F and the tip of the screw bears against the rear surface of electrode E1. Screw 50, when tightened, exerts pressure on the assembly formed by electrodes E1 and E2, membrane M and the centering rings to form a liquid tight assembly through which a sample is drawn. Preferably ring 37, membrane M and ring 37A are bonded together in a sandwich assembly to form a removable, disposable aperture unit U with the centering rings providing easy and convenient alignment. The cylindrical portions 25 and 25A of electrodes E1 and E2 constitute fittings which are received in the annular centering members or rings 37 and 37A.

Referring to FIG. 4, the signal elements produced at electrode E1 are supplied to an amplifier and discriminator portion 53 of the counting circuitry. Each signal element is supplied through a coupling capacitor C2 to a first amplifier stage 55 which includes an operational amplifier 57 and resistors R2 and R3. The amplified signal elements are then supplied through a filter comprised of coupling capacitor C3 and a resistor R4 to a second amplifier stage 58 which comprises an operational amplifier 59 and resistors R5 and R6. The output from the amplifier is supplied through a coupling capacitor C4 to a voltage divider 61 which is comprised of resistors R7 and R8. The divider output is supplied through a resistor R9 to one input of a comparator 63 (an operational amplifier). The other input to comparator 63, which is supplied through a resistor R10, is a voltage level developed across a potentiometer 65 whose setting determines the minimum size of detected particles in a sample drawn through the conduit which are counted. Thus, for example, if white blood cells in a sample of a patient's blood are to be counted, the potentiometer is set so that only particles whose size exceeds 4 microns, for example, are counted. The amplitude of each signal element supplied to voltage divider 61 varies the input level to comparator 63 from the divider and if this resultant level exceeds the threshold level established by the setting of potentiometer 65, a signal element of a first count signal is supplied by comparator 63 at its output.

Signal elements of the first count signal are supplied to a scaler 67 of count circuitry 68 and the scaler counts the signal elements and for each predetermined number of signal elements counted supplies a signal element of a second count signal. The scaler, which operates as is well known in the art is commercially available from Solid State Scientific, Inc. of Montgomeryville, Pennsylvania under their model designation SCL 4040A. Elements of the second count signal are applied to one input of a NAND gate G1 which has a second input to which is supplied a strobe signal by a calculator chip 69. Chip 69 is a 6-digit calculator chip the operation of which is well known in the art and the chip is commercially available from National Semiconductor Corp. of Santa Clara, California under their model designation MM 5736. The logic output of gate G1 is supplied to one input of a NAND gate G2 which has a second input to which is applied the logic output of a NAND gate G3. Gate G3 is controlled by the operation of reset switch 19 via manually operable valve V and has one input to which is applied a signal developed by an R-C circuit 71 comprised of a capacitor C5 and a resistor R11 when the switch is closed. The gate has a second input to which is applied a stobe signal from the calculator chip. Elements of the second count signal passed by gate G2 are supplied to an "add" input of calculator chip 69 which is responsive to each signal element to increment by one the contents of a counter within the chip. The number of second count signal elements counted by the calculator chip are supplied to a display 73 through a display control 75 which converts the binary value of the count to its decimal equivalent. The digital display includes a decimal point whose illumination is controlled by the calculator chip through an NPN transistor Q1 and resistors R12 and R13. Display control 75 is commercially available from National Semiconductor Corp. of Santa Clara, California under their model designation SN 75492. For the user's convenience the display is presented in readily interpretable units which are million cells/microliter.

The quantity of sample flowing through the conduit is precisely metered and this is accomplished by sensing the flow of sample through a predetermined length of the conduit and enabling the counting circuitry to count particles in the sample when it reaches the upstream end of the predetermined length and for inhibiting the counting circuitry from counting particles in the sample when it reaches the downstream end of the predetermined length. Since the diameter of the conduit is known, as is the predetermined length, the number of particles counted by the counting circuitry and the resultant display is for a predetermined volume of the sample.

An electrode E3 is positioned at the upstream end of the predetermined length and an electrode E4 is positioned at the downstream end thereof. The electrodes are identical in form, each being cylindrical in shape and having a longitudinal central bore whose diameter corresponds to that of the conduit. Electrode E3 is connected to battery 47 through a resistor R14 and to one input of a comparator 77 (an operational amplifier) through a resistor R15. Electrode E4 is also connected to battery 47. Prior to the leading edge of the sample reaching electrode E3, the voltage amplitude applied to the one input of comparator 77 is a first level. The comparator has a second input which is a reference level determined by the setting of a potentiometer 79. For the above initial condition, the level of the control signal exceeds that of the reference level. When the leading edge of the sample reaches electrode E3, a low impedace circuit path X1 is completed to ground through the medium and electrode E2. As a consequence, the level supplied to comparator 77 from electrode E3 falls below the reference level. When the leading edge of the sample reaches electrode E4, a second low impedance circuit path X2 is created, this path being between electrodes E3 and E4. The two circuit paths act as a voltage divider and as a result the voltage level supplied to the comparator from electrode E3 rises above the reference level. Whenever the level of the signal produced at electrode E3 falls below the reference level, a first control signal, which is a logic high, is produced by comparator 77. When the level exceeds the reference level, the comparator logic output goes low and a second control signal is produced by the comparator.

The logic output of comparator 77 is applied to both inputs of a NAND gate G4, which acts as an inverter, and to one input of a NAND gate G5 through an R-C network comprised of a capacitor C6 and a resistor R16. The logic output of gate G4 is applied to the reset input of scaler 67. Whenever a first control signal (a logic high) is supplied to gate G4, the gate supplies a logic low to scaler 67 which enables the scaler to count signal elements of the first count signal. When, however, a second control signal (a logic low) is supplied to gate G4, a logic high is applied to the reset input of the scaler which inhibits the scaler and resets the value of its contents to zero. Gate G5 has a second input which is a strobe signal supplied by calculator chip 69. The logic output of gate G5 is applied to both inputs of a NAND gate G6 and the logic output of this gate is supplied to the "1" input of the calculator chip.

It will be understood that metering electrodes E3 and #4 may alternatively be positioned upstream of sensing electrodes E1 and E2, with E3 adjacent electrode E2. In this configuration, operation of the counting and display circuitry is the same as that previously described except that generation of a first control signal occurs as the trailing end of the sample leaves electrode E4 and generation of a second control signal occurs as the trailing end of the sample leaves electrode E3. Thus the metering system of this apparatus will operate to correctly count without modification when the sample flow is reversed and the leading end or edge contacts in sequence electrodes E4, E3, E2 and E1.

Source 11 of negative pressure by which a sample is drawn through conduit 5 is a conventional disposable evacuated container 81. A puncturable membrane 83 stretches across the base of the container and the conduit has a lance-shaped outlet end 85. As shown in FIG. 1, the downstream end of conduit 5 has a 90° upward bend and frame F has a receptacle 87 formed in its upper surface and sized to receive container 81. Alternatively, as shown in FIG. 2, the downstream end of the conduit is straight and the receptacle is formed in the side of the frame so when in place, the container projects outwardly from the side of the frame. In either embodiment, insertion of the container into its receptacle results in membrane 83 being punctured by the lance end of the conduit. Now, each time manually operable valve V is opened, sample in well W is drawn off, by aspiration, through conduit 5 and the sample is collected in the container. When a container is full or no longer furnishes sufficient motive power to draw off a sample from the well, it is removed from its receptacle and disposed of in any convenient manner. Since disposal of the container also includes disposal of the samples which were aspirated through conduit 5, post-test clean-up is minimized. Further, the pressure differential created by the container vacuum prevents samples drawn into the container from flowing back into the conduit and lessens the possibility of contamination of later-drawn samples or of clogging.

Operation of the particle counter is as follows:

If, for example, a red blood cell count is being made, the user first takes a predetermined amount of a patient's blood and dilutes it in a saline solution, for example a 0.85% saline solution. A sample of the resultant suspension is then placed in well W and level L is manually depressed. This action flexes diaphragm 15 downwardly and opens the inlet end of the conduit. Concomitantly, the movement of the level closes reset switch 19 and a voltage is applied to R-C circuit 71. This results in a momentary high being applied to the one input of gate G3. The other input to gate G3 is periodically strobed by calculator chip 69, the strobe signal being a pulse supplied at a 1 kHz rate, for example, and producing a logic high at the gate input. With both inputs to gate G3 high, the gate supplies a logic low to gate G2. This forces the logic output of gate G2 high which clears the calculator chip contents. After a period determined by the time-constant of the R-C circuit, the one input to gate G3 goes low forcing the output of the gate high. This logic low input to gate G3 is maintained after level L is released and reset switch 19 reopens.

With level L depressed, the sample in well W is drawn off through conduit 5 and through aperture A in the membrane positioned between sensing electrodes E1 and E2. Each particle as it passes through the aperture, momentarily affects the conductivity of the circuit path established between the electrodes by the electrically conductive medium and results in a signal element being produced at electrode E1 and supplied to first amplifier stage 55 of the counting circuitry. The amplitude of each signal element produced at electrode E1 is a function of the size of the particle passing through aperture A and after a signal element has gone through two stages of amplification, it is supplied to comparator 63 through voltage divider network 61. If the signal amplitude exceeds the reference level, a signal element of the first count signal is produced by the comparator and supplied to scaler 67. Otherwise, no first count signal element is produced. Further, even if the size of a sensed particle exceeds the reference level so that a first count signal is produced, this signal element will not be counted by scaler 67 unless the leading edge of the sample flowing in the conduit has reached metering electrode E3, at which time a first control signal is supplied by comparator 77 thereby providing gate G5 with a logic high input from the comparator, the short duration of which is determined by the time constant of the R-C network. The other input to gate G5 is strobed by calculator chip 69 in the manner previously discussed and, when a strobe pulse appears at the respective input of the gate, the logic output of the gate goes low. This logic level is inverted by gate G6 and the resultant logic high supplied to the "1" input of the chip. Scaler 67 is enabled by the logic output of gate G4 and counts each signal element of the first count signal supplied to it. For every 128 signal elements counted by the scaler, for example, it supplies a signal element of the second count signal to gate G1 making the one input to the gate a logic high. The other input to gate G1 is strobed by the calculator chip 69 in the same manner as gate G3 and when a strobe pulse is applied to gate G1 both its inputs are logic high and its logic output goes low. Because the logic output of gate G1 to the one input of gate G2 is by now high, the logic low supplied to the other input of gate G2 by gate G1 forces the logic output of gate G2 high, this high being supplied to the "add" input of the chip incrementing the contents of an internal register by one and displays the result as a digital number at display 73. This continues until the leading edge of the sample reaches electrode E4 at which time scaler 67 is inhibited and, although particles larger than the predetermined minimum size may be sensed in the remaining portion of the sample, no more second count signal elements are generated and the number displayed is not changed. When the last of the sample is drawn off from well W, level L is released and returns to its initial position. As previously discussed, however, this does not affect the logic input to gate G3 which is already low due to the operation of R-C network 71.

In the event aperture A in membrane M becomes clogged due to clotted particles or debris in a sample, the flow system may be backflushed utilizing a hypodermic syringe. To do this, container 81 is removed from its receptacle 87 and the end of the syringe is inserted over the downstream end 85 of the conduit. The syringe is fitted with a rubber washer or gasket to form a seal between the body of the syringe and the surface of receptacle 87. After depressing level L to open the inlet end of the conduit, the plunger of the syringe is depressed to force air, and if desired, a washing solution back through the conduit. The lever is then released, the syringe removed and a new evacuated container is installed in receptacle 87. If the clogging condition is not remedied by the above procedure, centering ring-membrane assembly 37, M, 37A may be quickly and easily removed and replaced as a unit. To do this the screw 50 is loosened and this permits electrode E1 to be moved away thereby permitting removal and discarding of the unitary aperture assembly unit U from its position between the sensing electrodes. A new aperture assembly unit is inserted in place of the old one and electrode E1 is moved back to its original position. It will be noted that this unit is self-centering which is important to insure precise alignment particularly where as here conduit 5 is very narrow as it should be in portable equipment. Screw 50 which serves as a clamping means is then tightened to again form a liquid-tight assembly.

An important advantage of apparatus of this invention is that, except when in use, the conduit can be kept completely filled with a hemolyzing, bacteriostatic and fungistatic or bactericide and fungicide solution. Thus the fluid system can be kept sealed with the valve V closed between usages thereof.

Figure 5:
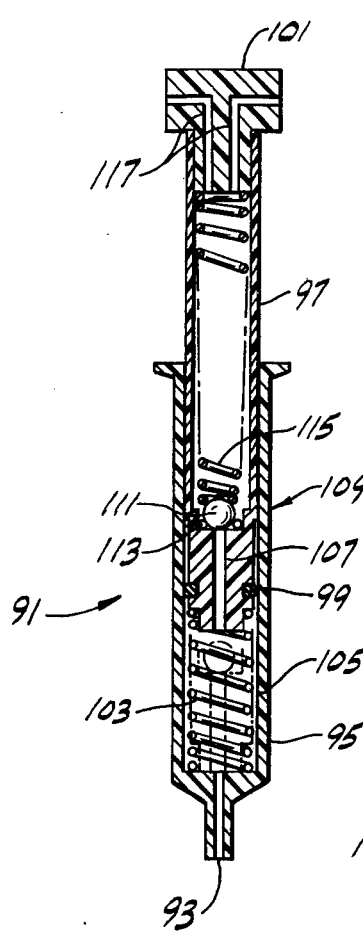
FIG. 5 is a longitudinal section of a source of motive power for the apparatus.

Referring to FIG. 5, a rechargeable vacuum source or "thumb pump", generally indicated at 91, has an inlet 93 removably attached to the outlet end of the conduit. The thumb pump is usable in place of evacuated container 81 as a source of motive power to draw a sample through the conduit and it also collects sample drawn through the conduit for easy and safe disposal of the collected material. The pump comprises a cylinder 95 one end of which communicates with the pump inlet and a piston 97 slidable within the cylinder. An 0-ring 99 fits around the piston to form a sliding seal between the piston and the cylinder. The piston is hollow and is capped by a plug 101. The piston is movable from a retracted position (the solid-line position shown in FIG. 5) to an extended position (the dashed-line position shown in FIG. 5) when manual force is applied to the capped end of the piston. This movement actuates the pump to charge it, and a spring 103 disposed in the cylinder biases the piston toward its retracted position. A chamber 105 is formed by the piston and the cylinder, and a passage 107 provides communication between the hollow portion of the piston and the chamber.

A ball check valve 109 closes one end of the passageway and consists of a ball 111 biased against an 0-ring 113 by a spring 115 disposed in the hollow portion of the piston. During the initial stroke of the piston when the pump is charged, check valve 109 if forced open and air and sample material previously drawn through the conduit is forced through the passageway 107 into the piston. A small amount of fluid, however, may be forced back through the conduit and membrane assembly to backflush the fluid flow sytem, valve V then being opened briefly. Again, this clears the conduit of obstructions and prevents clogging. A partial vacuum is created in chamber 105 as a result of the charging operation and the resultant negative pressure acts as a motive source to draw a sample through the conduit when manually operable valve V is next opened. After a number of charging operations, piston 97 will fill with collected sample material. When this occurs, pump 91 is removed from its position and inverted over a suitable waste receptacle. A pair of drain passages 117 formed in plug 101 communicate with the hollow piston and the atmosphere. The collected sample material flows out of these drain passages into the receptacle and, after emptying the contents of the plunger, the pump is reinstalled and charged for subsequent particle count operations.

Pump 91 has several advantages over the evacuated container or negative pressure source 11 in that pump 91 may be recharged while installed in the counter and its liquid accumulator can easily be emptied simply by inverting it. Also many more samples can be counted before emptying is required because air can be vented through passages 117 as liquid accumulates in chamber 105. Additionally the flush back pressure which is applied through the flow tube or conduit 5 to aperture A has been found to reduce plugging or clogging as compared to usage of the pre-evacuated container 11 under similar conditions.

Figure 8:
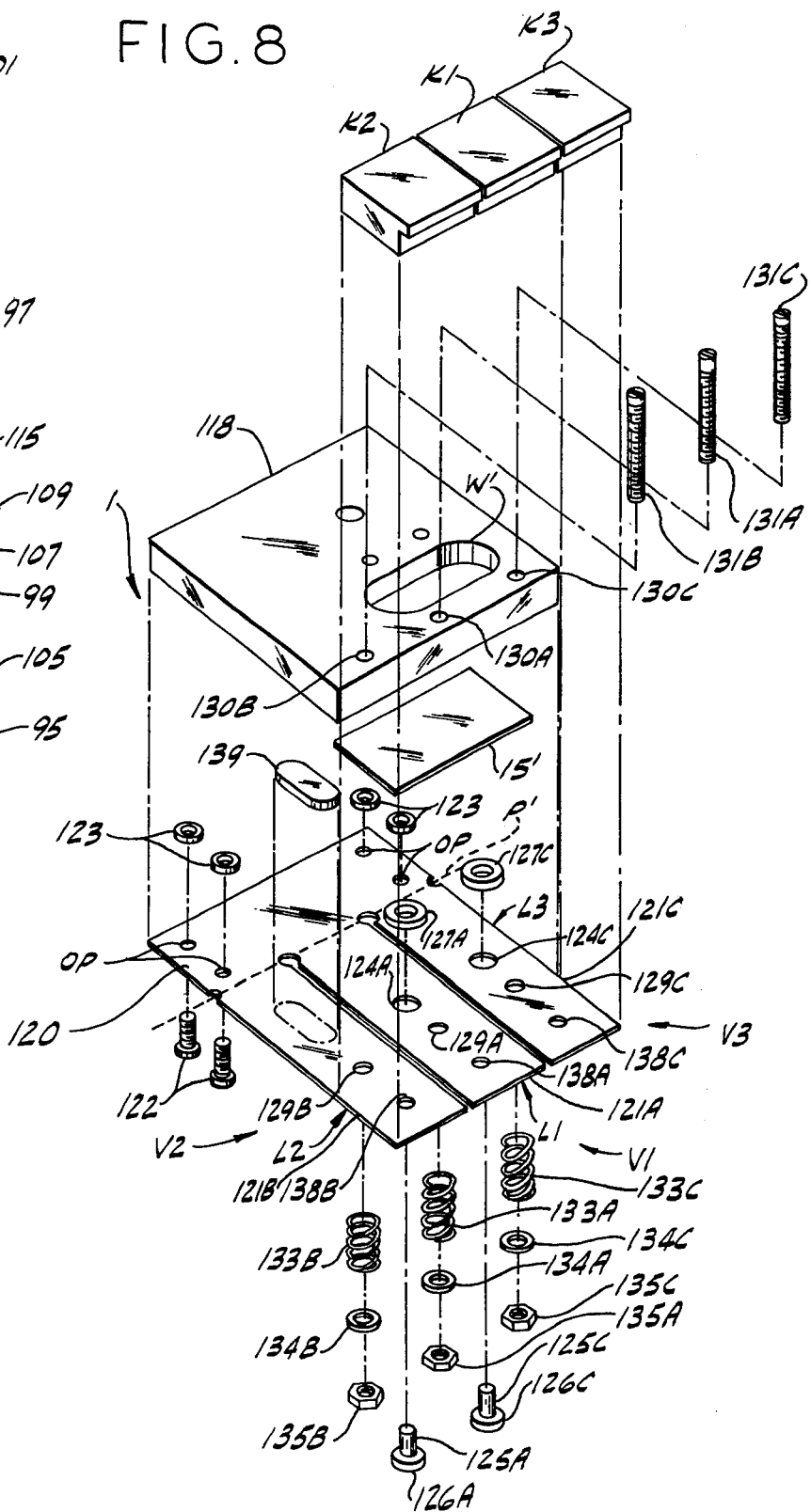
FIG. 8 is an exploded view of a portion of a second embodiment of the invention illustrating the valving assembly thereof.

Referring to FIGS. 6, 7 and 8, a second embodiment of a particle counter of the invention is indicated generally at 1' and has a well W' in which a sample is placed and a conduit 5' through which the sample is drawn for collection in pump 91. Although a thump pump is shown in FIG. 6 as the source of negative pressure, it will be understood that an evacuated container 81 may also be used for drawing and collecting sample material. Samples flow through conduit 5' sequentially past metering electrodes E4', E3' and then sensing electrode E2', then through an aperture A' in a membrane M' that is sandwiched between the electrodes, and finally sensing electrode E1'. Thus electrodes E1' and E2' are downstream from metering electrodes E4' and E3'. A flow regulator 119 is inserted in conduit 5' to regulate flow of a sample between inlet end 9' of the conduit and pump 91. The bottom of well W' is a flexible diaphragm 15' movable by a lever L1 from a conduit-closing to a conduit-opening position when a key K1 at one end of the lever is depressed.

As shown in FIGS. 7 and 8, well W' is formed in a block 118 of a synthetic resin material, such as that sold under the trademark "Lucite" by E. I. du Pont de Nemours & Co., and diaphragm 15', of a suitable elastomer material such as rubber, is attached around its margins to the underside of the block to form the bottom of the well. A plate 120 has three fingers 121A-121C, and openings OP are formed in the plate for attaching the plate to the underside of block 118 by screws 122 and spacers 123. Threaded bores (not shown) are formed in the underside of block 118 in registry with opening OP for receiving screws 122. When attached to block 118, fingers 121A-121C project outwardly and each finger is movable as a cantilever about a pivot indicated by the dashed line P'. Finger 121A has an opening 124A in registry with the inlet end 9' of conduit 5'. A pin 125A has one end secured to the underside of diaphragm 15' and projects through opening 124A. An enlarged head 126A of the pin is spaced beneath the underside of finger 121A and is moved downwardly when key K1 is depressed. A spacer 127A fits over the shaft of the pin.

Finger 121A has a second opening 129A intermediate opening 124A and the free end of the finger. In alignment with opening 129A is a threaded bore 130A formed in block 118. A post 131A is threaded into bore 130A and projects through opening 129A so that a portion of the post extends beneath finger 121A. A spring 133A is carried by the shank portion of post 131A beneath the finger with the spring reacting between the underside of the finger and a seat constituted by a washer 134A held captive on post 131A by a nut 135A. The upward biasing force of this spring against the underside of lever 121A is adjusted by rotation of post 131A clockwise or counterclockwise, post 121A having a slotted upper end of reception of a screwdriver for effecting this rotation. Key K1 is attached to the free end of finger 121A, there being an opening 138A at the free end of the finger for this purpose. The completed assembly forms a valve V1 for opening the inlet end of conduit 5' for aspiration of a sample from well W' through the conduit. A lever L1 of the valve is comprised of finger 121A and when key K1 is manually depressed finger 121A moves downwardly against the force of spring 133A to move pin 125A and flex diaphragm 15' away from the inlet end of the conduit. A switch 19' (FIG. 7) is positioned beneath lever L1 and actuator 21' of the switch is engaged by the lever as it moves downwardly to close the switch and reset the counting means to enable the counting means to count particles in the next sample flowing through the conduit.

Conduit 5' may be vented to the atmosphere to interrupt the flow of a sample through the conduit. An opening or port 137 (FIG. 6) is formed in the underside of the conduit and a closure pad 139 (FIGS. 6 and 8) for the port is carried by a lever L2 of a valve V2 for opening and closing the port. Lever L2 is comprised of finger 121B of plate 120, the finger having an opening 129B at a location similar to that of opening 129A in finger 121A. A post 131B, spring 133B, washer 134B and nut 135B are assembled in the same manner as previously described for valve V1 and a key K2 is attached to the free end of finger 121B. When lever L2 is at a port closing position, pad 139 presses against opening 137 to close the port. When lever L2 is depressed by applying manual force to key K2, finger 121 moves against the force of spring 133B to move pad 139 away from the opening and expose the conduit to atmospheric pressure. Air is then drawn into the conduit and the flow of sample upstream from opening 137 ceases. This continues until key K2 is released and the port is again closed. Flow of the remaining sample through the conduit resumes and a slug of air separates the two portions of the sample. It will be understood that the above-described sequence may be repeated until all of the sample in the well has been drawn off into the conduit. As a result of the above, multiple sample portions may be drawn from a single sample and a particle count obtained for each sample portion.

To obtain a particle count for each portion of the sample, reset switch 19' is positioned beneath lever L2 and an on/off switch 141 (see FIG. 9) is positioned beneath lever L1. Switch 141 is also a microswitch and has an actuator engaged and depressed by lever L1 when the lever is depressed. Further, lever L1 has a latching finger (not shown) which is engaged by a latch (also not shown) when the lever is depressed to keep the lever depressed and the on/off switch actuated. Since depression of lever L1 opens the inlet end of conduit 5', sample in well W' is drawn into and through the conduit. When the leading portion of the sample is visible at the base of thumb pump 91, key K2 is depressed to open port 137 and draw air into the conduit. At the same time, reset switch 19' is actuated and counting circuitry 13 is reset. When the leading edge of the slug of air (the trailing edge of the sample) leaves metering electrode E4', the counting circuitry begins counting particles in the manner previously described. When the leading edge of the air slug (the trailing end of the sample) passes leaves the other metering electrode, counting of particles is terminated and the particle count is displayed on display 73'. When key K2 is released, lever L2 returns to its initial position and port 137 is closed and sample in conduit 5' upstream from the port resumes flowing through the conduit. If conduit 5' is again vented, enabling and inhibiting of the counting circuitry for the particle count again occurs on the leading edge of the air slug introduced into the conduit respectively leaving electrodes E4' and E3'. If the conduit is not vented again, control of the counting circuitry occurs on the trailing edge of the remaining sample leaving the respective metering electrodes. After all the samples has been aspirated from well W', lever L1 is released by releasing its latch and the lever returns to its normal position. On/off switch 141 is deactuated by this action and power is removed from the counting and display circuitry.

After a sample has been aspirated from the well, a washing solution may be introduced into the well to cleanse it. The washing solution is drawn from the well through a conduit 143 (FIG. 6) which has an inlet end 145 normally closed in the same manner as is the inlet end of conduit 5', i.e., the inlet end of this second conduit extends down into well W' to the bottom of the well and the inlet end is fixed while the bottom of the well, the flexible diaphragm, is movable relative to the inlet end from a conduit-closing to a conduit-opening position. The source of motive power for drawing off washing solution through this second conduit is pump 91, and the outlet end of conduits 5' and 143 commonly empty into a tapered hole or receptacle 147 in which the inlet of pump 91 or an evacuated container 81 (if a tube 85 and a receptacle 87 is provided) is received. Opening of the inlet end of conduit 143 is accomplished in the same way as is the opening of the inlet end of conduit 5', i.e., a lever L3 whose construction is the same as that previously described for lever L1 is movable about the pivot when manual force is applied to a key K3 on the free end of the lever. When the lever is depressed, the diaphragm flexes downwardly, opening the inlet end of the conduit. After the washing solution has been aspirated from the well, key K3 is released and the lever returns to its original position. The diaphragm again presses against and closes the inlet end of the conduit.

Figure 9:
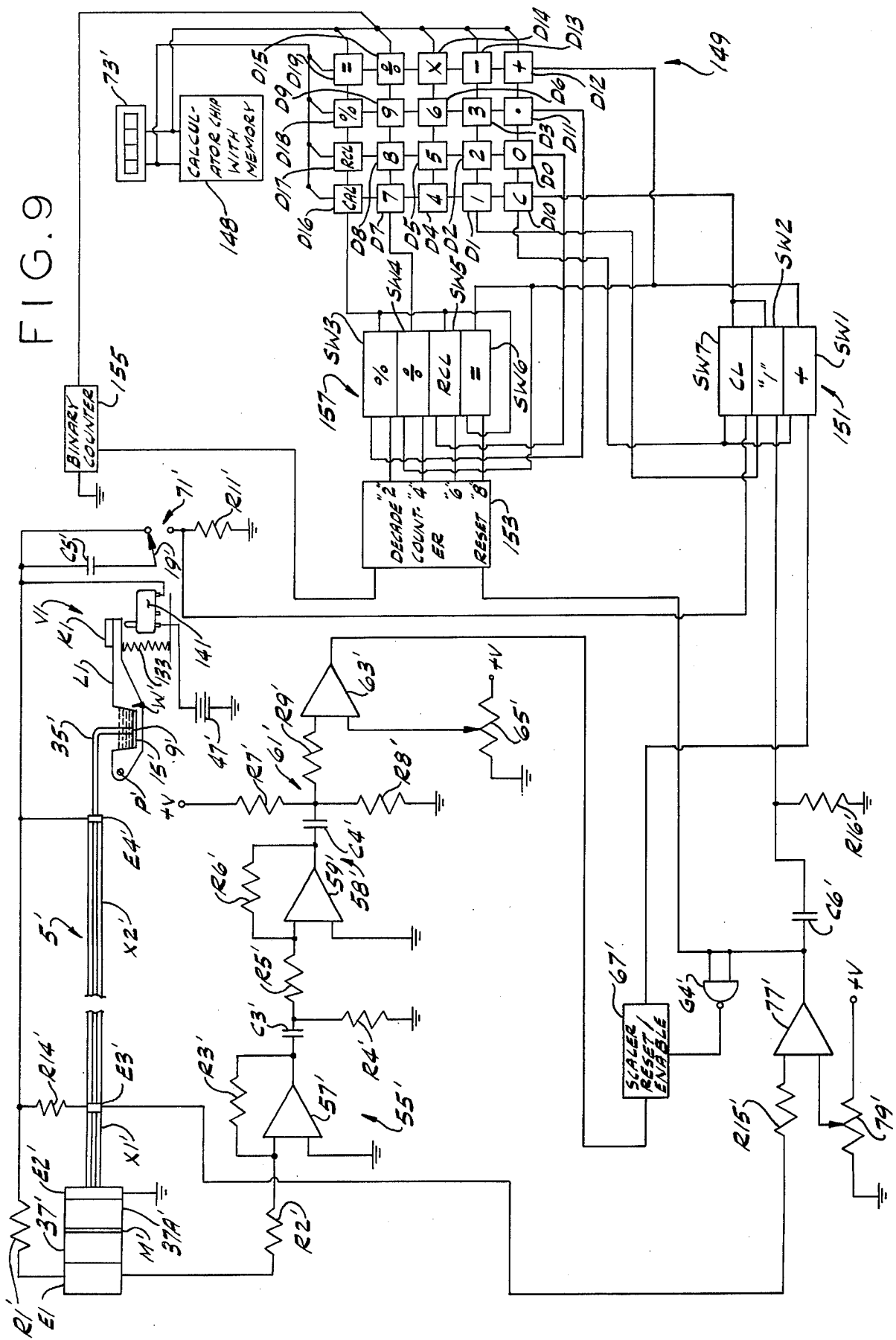
FIG. 9 is a schematic circuit diagram of a second embodiment of particle counting circuitry of the apparatus.

Referring to FIG. 9, a second embodiment of the particle counting and display circuitry for a particle counter of the present invention is schematically represented. This embodiment includes a calculator chip 148 capable of performing mathematical operations and having a memory for storing usable data and the results of these operations. A keyboard 149 includes a plurality of data and instruction keys D0 - D19 by which data and operating instructions are supplied to the calculator chip in a manner well known in the art and as, for example, described in "the Small Electronic Calculator", Eugene W. McWhorter, *Scientific American*, March 1976, pages 88-98.

The metering and sensing portions of the counting circuitry are the same as previously described with reference to FIG. 4, except that metering electrodes E3' and E4' are positioned upstream from sensing electrodes E1' and E2'. Electrode E4' is connected directly to battery 47' when switch 141 is closed, while electrode E3' is connected to the battery through a resistor R14'. Electrode E2' is grounded and electrode E1' is connected to the battery through a resistor R1' and switch 141, and to amplifier 55' through a resistor R2'. Operation of the sensing and metering electrodes is similar to that previously described with elements of the first count signal produced at electrode E1'. Elements of a first count signal are supplied to scaler 67' which produces an element of the second count signal for every predetermined number, e.g. 128, first signal elements supplied to it from comparator 63'. Scaler 67' is enabled by a logic low from gate G4' when the logic output of comparator 77' goes high, this occuring when the trailing end of a sample leaves metering electrode E4'. Elements of the second count signal are supplied to one input of a bilateral switch SW1 which is contained on an integrated circuit chip 151. Chip 151 is commercially available from Solid State Scientific Inc., Montgomeryville, Pennsylvania, under their model designation SCL 4016A and contains four bilateral switches each of which has two input terminals and one output terminal. The logic output of comparator 77 is also supplied to one input of a second bilateral switch SW2 contained on chip 151 through the R-C network comprised of resistor R16' and capacitor C6' and to the reset input of a decade counter 153. The decade counter is supplied with clock pulses by a binary counter 155 which is driven by a strobe signal from calculator chip 148. Decade counter 153 supplies a logic output to one input terminal of each of four bilateral switches SW3 - SW6 respectively contained on an integrated circuit chip 157, chip 157 being identical to chip 151 and available from the same source. Decade counter 153 is also commercially available from Solid State Scientific Inc. of Montgomeryville, Pennsylvania, under their model designation SCL 4017, as is binary counter 155 under the company's model designation 4040A. Use of the bilateral switches on chips 151 and 157, decade counter 153 and binary counter 155 permits instructions controlled by certain keys on keyboard 149 to be automatically as well as manually generated and supplied to calculator chip 148, thereby to control arithmetic operations performed by the calculator chip.

Specifically, a bilateral switch SW7 and bilateral switch SW1 on chip 151 respectively control "clear" and "+" instructions to the calculator chip, and switch SW2 controls the number "1". Bilateral switches SW3 - SW6 on chip 157 respectively control "%", "÷", "RCL" and "=" instructions to the calculator chip. Each switch on each chip has as one input a strobe signal supplied by the calculator chip. The other input to "clear" switch SW7 on chip 151 is connected to the output of R-C network 71'. The second input to each of the switches on chip 157 is connected to one of the output terminals of decade counter 153 for reasons to be discussed. The output of each switch on both chips is connected to an input of calculator chip 148.

It is sometimes desirable, for example, for perform a particle count on a sample of a reference cell suspension, i.e., a suspension having a known quantity of particles per given volume, prior to performing a particle count on other samples. With the particle counting circuitry of FIG. 9, a conversion factor is readily computed for the reference suspension which is then used to calculate the actual particle count of subsequent samples. If, for example, the nominal value for the reference cell suspension is 4.55 million erythrocytes per microliter, the value 4.55 is entered into the memory portion of chip 148 by sequentially depressing keys D4 and D11, the key D5 twice and then "store" key D16. The reference cell suspension is then diluted in isotonic saline in a ratio of approximately 1:50,000, for example, and a sample of the dilution is placed in well W'.

When lever L of manually operable valve V is depressed to open the inlet end of conduit 5, reset switch 19 is actuated and a momentary logic high is supplied from R-C network 71' to one input of bilateral switch SW7 on chip 151. When the other input to switch SW7 is strobed by the calculator chip, the switch applies a "clear" signal to the chip to clear the contents of its count register. When the trailing end of the reference sample leaves metering electrode E4', the logic output of comparator 77' goes high, as previously discussed, enabling scaler 67', and momentarily lifting one input of switch SW2 high and entering a "1" into the calculator. Scaler 67' supplies a signal element of a second count signal for every 128 signal elements of the first count signal supplied to it. Each second count signal element is supplied to one input of bilateral switch SW1 and when the other input to switches SW1 and SW2 is strobed by calculator chip 148, the internal register in the chip is incremented by one. When the trailing end of the reference sample leaves metering electrode E3' the logic output of comparator 77' goes low inhibiting scaler 67' from supplying further signal elements of the second count signal. Further, the logic high-to-low transition at the comparator output resets decade counter 153.

As noted, decade counter 153 is responsive to timing pulses supplied by binary counter 155 in response to strobe signals received by the binary counter from calculator chip 148. When the contents of the decade counter reach "2", a logic high is supplied by the decade counter to one input of bilateral switch SW3 on chip 157. When the other input to switch SW3 is strobed by the calculator chip, a "%" instruction is supplied to the calculator chip. When the contents of the decade counter reach "4", a logic high is supplied to one input of bilateral switch SW4, and when the other input to the switch is strobed, a "÷" instruction is supplied to the calculator chip. Similarly, when the contents of the decade counter reach "6" and "8" respectively, a "recall" and an "=" instruction are respectively supplied to the calculator chip. In response to the sequentially supplied set of instructions, the calculator chip recalls the reference value 4.55 stored in its memory. The number of second signal elements counted multiplied by the factor 0.0D is divided by this number, and the result is displayed. If, for example, the number of second count signal elements counted were 366, the resultant display would be 0.8043956. This value, which is a conversion factor, is now entered into the calculator chip memory by depressing key D16 which controls the "store" function of the calculator and is labeled "CAL" to indicate its calibration function.

Particle counts for any number of additional samples may now be made with the particle count displayed being equal to the number of signal elements of the second count signal which are counted, divided by the conversion factor stored in the calculator chip memory.

Operation of the particle counter is the same as above described in that signal elements of the second count signal are generated by scaler 67' as a sample flows through conduit 5 and the number of such signal elements are counted by calculator chip 148. When the trailing end of a sample leaves metering electrode E3', scaler 67' is inhibited and decade counter 153 reset. The sequence of instructions previously described is then generated and the conversion factor stored in the calculator chip memory is recalled, divided into the count value and the result displayed. Thus, in the present example, if 421 second signal elements are counted for a subsequent sample, this number is automatically divided by the previously stored conversion factor 0.8043956 and the result is displayed as 5.23 million cells per microliter. The same conversion factor remains in the calculator chip memory until power for the counter is turned off or the memory is cleared. It will be understood that this calibration factor may be reentered into the memory or manually entered as a divisor when the counter is again used.

By employing the particle-counting circuitry of FIG. 9 in the manner above described, the metering system of particle counters of the present invention may vary slightly from unit to unit without affecting the accuracy of the actual particle count values obtained with each unit. Further, the dilution of each sample for which a particle count is made need not be a specific value so long as the reference cell suspension used to calibrate the counter is diluted to the same extent as the samples subsequently counted by a counter. This permits samples to be diluted using a simple, uncalibrated pipette provided the same pipette is used to dilute the reference cell suspension and each sample subsequently counted by the same counter.

As described above, in the embodiment of FIG. 9 and the apparatus of FIG. 6, the metering electrodes E3', E4' are positioned upstream of the sensing electrodes E1', E2'. Several advantages are achieved by this arrangement. For example, as the metering electrodes E3', E4' are located on the low pressure side of the aperture in the counting system if there is any tendency for bubble formation, this will evidence itself on the liquid fronts. This is because the aperture itself is most frequently the cause of any bubble formation. Since the metering system is located upstream of the aperture any bubbles caused by the aperture will not be present in the metering system. Thus, as the trailing end of the sample, rather than the leading edge, triggers the control circuit when the metering electrodes are upstream of the counting electrodes consistent conductivity triggering of the control circuit and therefore more precise volume metering results. Also, during the counting period the rate of flow through aperture A is stabilized by the fact that as the column of liquid decreases in length when the trailing end moves from electrode E4' to electrode E3' (the counting period), the force needed to pull it decreases since there is less friction between the liquid and the inner side of flow tube or conduit 5' as the liquid column becomes shorter while at the same time the pressure when using pre-evacuated tube 81 decreases as more liquid enters tube 81 as the counting proceeds. Therefore, these two effects contribute to a more stable and even flow during the counting period that when the metering system is located downstream to the aperture. Thus, an even flow during the counting period may be achieved without the use of a flow regulator, if desired.

In view of the above, it will be seen that the several objects of the invention are achieved and other advantageous results attained.

As various changes could be made in the above constructions and methods without departing from the scope of the invention, it is intended that all matter contained in the above description or shown in the accompanying drawings shall be interpreted as illustrative and not in a limiting sense.

What is claimed is:

1. Apparatus for counting particles, such as blood cells, suspended in a liquid medium, comprising:
   a chamber for receiving a sample of the liquid medium containing suspended particles;
   a conduit for flow of the sample from the chamber;
   means normally closing the conduit adapted to be opened for flow of the sample therethrough;
   means for drawing the sample through the conduit concurrently with opening of said conduit-closing means;
   means for counting particles in the sample as it flows through the conduit; and
   manually operable means for opening said conduit-closing means for flow of a sample therethrough and concomitantly actuating the counting means to count the particles in the sample flowing through the conduit.

2. Apparatus as set forth in claim 1 wherein said drawing means comprises a source of negative pressure.

3. Apparatus as set forth in claim 2 wherein said source is an evacuated container to which said conduit is connected, said container receiving the drawn-off sample after the particle count.

4. Apparatus as set forth in claim 2 wherein the conduit has an outlet end and the source of negative pressure is a pump having an inlet for attachment thereto.

5. Apparatus as set forth in claim 4 wherein the pump comprises a cylinder one end of which communicates with the pump inlet, a piston slidable in the cylinder between a retracted position and an extended position and manually operable means for moving the piston from said retracted position to said extended position to actuate the pump.

6. Apparatus as set forth in claim 5 wherein a second chamber is formed by the cylinder and the piston, a check valve for said second chamber, said check valve opening when the pump is actuated to vent air from said second chamber to the atmosphere.

7. Apparatus as set forth in claim 6 wherein the pump further includes a spring biasing the piston toward its retracted position when the manually operable means is released whereby a vacuum is created in the second chamber for drawing the sample through the conduit when said conduit-closing means is opened, the sample drawn through the conduit being collected in said second chamber.

8. Apparatus as set forth in claim 7 wherein the piston is hollow and has a first passage in communication with the second chamber and a second passage in communication with the atmosphere, said check valve being positioned at one end of said first passage whereby a sample collected in the second chamber is admitted into the piston through said first passage when the pump is actuated and discharged from the piston through said second passage when the pump in inverted.

9. Apparatus as set forth in claim 1 wherein the chamber is in the form of a well open at the top for receiving the sample and having a bottom, and wherein the conduit has an inlet end extending down into the well toward its bottom, the bottom of the well and the inlet end of the conduit being relatively movable between a closed position wherein the bottom closes said inlet end and an open position wherein said inlet end and bottom are spaced for entry of the sample into the conduit.

10. Apparatus as set forth in claim 9 wherein the inlet end of the conduit is fixed and the bottom of the well is flexible and adapted to flex from said conduit-closing position in which said bottom engages the inlet end of the conduit to said conduit-opening position.

11. Apparatus as set forth in claim 10 wherein the bottom of the well comprises a flexible diaphragm and the manually operable means includes means for flexing the diaphragm.

12. Apparatus as set forth in claim 11 wherein the flexing means comprises a lever for flexing the diaphragm to said conduit-opening position when a manual force is applied to one end thereof, and a spring biasing the lever toward said conduit-closing position.

13. Apparatus as set forth in claim 12 wherein the counting means includes a switch actuable by the lever when the diaphragm is moved into said conduit-opening position for resetting the counting means to enable it to count the particles in the next sample to flow through the conduit.

14. Apparatus as set forth in claim 13 wherein said counting means includes circuitry, said switch supplying power to said circuitry only while said switch is actuated by the diaphragm when in its conduit-opening position.

15. Apparatus as set forth in claim 1 which further includes manually operable means for venting the conduit to the atmosphere to interrupt flow of the sample through the conduit.

16. Apparatus as set forth in claim 15 wherein the venting means includes a port for the conduit and means for selectively opening and closing the port.

17. Apparatus as set forth in claim 16 wherein the port is constituted by a hole in the conduit and the opening and closing means comprises a closure for the hole carried by a lever which moves the closure away from the hole to a port-opening position when manual force is applied to one end of the lever, and a spring biasing the lever toward a port-closing position at which the closure covers the hole.

18. Apparatus as set forth in claim 17 wherein the counting means includes a switch actuable by the lever when the closure is moved toward the port-opening position for resetting the counting means whereby successive applications of manual force to the lever introduce successive slugs of air into the conduit to separate the sample flowing therein into successive portions and the counting means is reset upon each actuation of the switch by movement of the lever to count particles in each respective portion of the sample.

19. Apparatus as set forth in claim 1 further including means for discharging a washing solution from the chamber, said washing solution being introduced into the chamber after a sample has been drawn from the chamber through the conduit.

20. Apparatus as set forth in claim 19 wherein the chamber is constituted by a well open at the top and having a bottom, and the discharging means includes a second conduit through which the washing solution is drawn from the well by the drawing means, said second conduit having an inlet end extending down into the well toward the bottom, and the bottom of the well and the inlet end of the second conduit are relatively movable between a closed position wherein the bottom closes said inlet end and an open position wherein said inlet end and bottom are spaced apart for entry of the washing solution into the second conduit.

21. Apparatus as set forth in claim 20 wherein the inlet end of said second conduit is fixed and the bottom of the well is a flexible diaphragm and the manually operable means includes a lever for flexing the diaphragm to said conduit-opening position when manual force is applied to one end of the lever, and a spring biasing the lever toward said conduit-closing position.

22. Apparatus as set forth in claim 1 wherein the counting means includes means for detecting particles in the sample as it flows through the conduit and for producing an electrical signal indicative of the particles detected.

23. Apparatus as set forth in claim 22 wherein the medium in which the particles are suspended is electrically conductive and the detecting means includes means for completing an electrical circuit path through the sample as it flows through the conduit, the conductivity of said path being varied by particles in the sample to produce the electrical signal.

24. Apparatus as set forth in claim 23 wherein the conduit has an inlet end and the detecting means includes a pair of electrodes positioned downstream from said inlet end, each electrode being adapted for flow of sample therepast and for connection to a source of electrical energy whereby said electrical circuit path is completed between the electrodes through the sample when it is simultaneously flowing past both electrodes, and an electrically non-conductive member positioned between the electrodes and having an aperture therein sized to permit particles in the sample to pass therethrough, passage of a particle through the aperture momentarily affecting the conductivity of the electrical circuit path between the electrodes and producing a signal element of the electrical signal.

25. Apparatus as set forth in claim 24 wherein the counting means includes means for amplifying the signal elements produced by the detection means and means for comparing the amplitude of each amplified signal element with a predetermined reference level the amplitude of which is a function of the size of particles in the sample which are to be counted to produce an element of a count signal for each amplified signal element exceeding the reference level.

26. Apparatus as set forth in claim 25 wherein the counting means further includes a counter for counting the number of count signal elements produced, the contents of said counter being a function of the number of particles in the sample exceeding a predetermined minimum size.

27. Apparatus as set forth in claim 26 wherein the counting means further includes scaling means for counting elements of the count signal produced by the comparing means and for supplying an element of a second count signal to the counter for each predetermined number of count signal elements counted, the contents of said counter equalling the number of second count signal elements supplied thereto.

28. Apparatus as set forth in claim 24 in which said member comprises a membrane and which further includes means for releasably securing the non-conductive membrane between the electrodes so the membrane may be replaced if its aperture becomes clogged or damaged.

29. Apparatus as set forth in claim 28 wherein said means for releasably securing the non-conductive membrane between the electrodes includes centering means bonded to the opposite surfaces of said membrane whereby the membrane and centering means may be removed and replaced as a unit which is self-centering.

30. Apparatus as set forth in claim 29 in which said centering means comprises centering members bonded to each of the two opposite surfaces of said membrane and having a passage therethrough, a first fitting having a passage communicating with the inlet end of the said conduit and a second fitting communicating with the outlet end of said conduit, each fitting being relatively movable toward and away from each other, means for clamping as a unitary assembly said bonded members and membrane between said fittings by moving said fittings toward each other, said fittings and said centering members having mating configurations whereby the members when clamped between said fittings are positioned with the passages in said fittings and centering members all in communication with the aperture.

31. Apparatus as set forth in claim 30 wherein each of the fittings includes one of said electrodes.

32. Apparatus as set forth in claim 31 wherein said fittings constitute said electrodes and the axes of said passages in said fittings and said centering members are coaxially aligned with said aperture.

33. Apparatus as set forth in claim 32 wherein the centering members are annular in shape and the electrodes are cylindrical with the inner dimensions of the passages in the centering member being only slightly greater than the outer dimensions of the electrode whereby the unitary assembly of said bonded members and membrane is easily replaced when the fittings are moved apart and are self-centered upon the fittings being moved together when reclamping.

34. Apparatus as set forth in claim 1 further including means for displaying the number of particles counted by the counting means as a visual indication of the particle count.

35. Apparatus as set forth in claim 1 wherein the counting means includes means for establishing a calibration factor and for factoring the number of particles counted by said calibration factor to produce a number representative of the actual particle count for the sample.

36. Apparatus as set forth in claim 35 wherein the calibration means comprises means for generating a value equal to the number of particles in a predetermined volume of a reference sample which is received in the chamber and drawn through the conduit and memory means for storing said value.

37. Apparatus as set forth in claim 36 wherein the memory means is contained on a calculator chip and the generating means includes a keyboard having a plurality of manually operable keys by which numbers and operating instructions are generated and supplied to the chip, said value being generated by depressing numerical keys on the keyboard and stored in the memory means by depressing an appropriate instruction key.

38. Apparatus as set forth in claim 37 wherein the calibration means further includes sequencing means responsive to the termination of the counting of particles in the reference sample for recalling the value from the memory means and dividing said value into the actual particle count for the reference sample thereby to produce said calibration factor which is then stored in the memory means, said sequencing means being further responsive to the termination of the counting of particles in a sample later drawn through the conduit to sequentially supply instruction signals to the calculator chip in a sequence by which the calibration factor is recalled from the memory means and the particle count for said sample is divided thereby to produce the number representative of the actual particle count for the sample.

39. Apparatus as set forth in claim 1 wherein the medium in which particles are suspended is electrically conductive and which further includes metering means for accurately determining a sample volume equal to that in which the particles are to be counted, said metering means including a length of the conduit which is substantially electrically nonconductive, first and second electrodes spaced apart a predetermined distance along said conduit for being sequentially contacted by said sample as it passes therethrough, means responsive to an end of the sample passing the first contact to initiate the counting of particles, and means responsive to the same end of the sample passing the second contact to terminate the counting of particles whereby the number of particles counted represents those contained in a volume of sample equal to that present in the length of conduit between said electrodes.

40. Apparatus as set forth in claim 39 wherein said means for initiating and terminating the counting of particles includes means for sensing a change in the conductivity of the path in said conduit length between the first and second electrodes.

41. Apparatus as set forth in claim 39 in which the means for initiating and terminating the counting of particles further includes a third electrode for being contacted by said sample, said third electrode being positioned along said conduit length and adjacent the second electrode, and means for sensing changes in the conductivity between said first and second electrodes and in the conductivity between said second and third electrodes whereby as an end of the sample passes said first, second and third electrodes the conductivity of the paths between said first and second and the second and third electrodes will sequentially change thereby to produce a first control signal to initiate counting and a second control signal to terminate counting.

42. Apparatus as set forth in claim 41 wherein the first and second electrodes are positioned upstream from the third electrode with the trailing end first passing the first, second and third electrodes in that order whereby the first control signal is produced by the trailing end of the sample as it leaves the first electrode and the second control signal is produced as the sample's trailing end leaves the second electrode.

43. Apparatus as set forth in claim 41 wherein the first and second electrodes are positioned downstream from the third electrode with the leading end of the sample passing the third, second and first electrodes in that order whereby the first control signal is produced by the leading end of the sample reaching the second electrode and the second control is produced by the leading end of the sample reaching the first electrode.

44. Apparatus as set forth in claim 1 further including a portable frame in which the chamber, conduit, conduit-closing means, particle-counting means and manually operable means are mounted and to which the drawing means is removably attached.

45. Apparatus for counting particles, such as blood cells, suspended in an electrically conductive liquid medium, comprising:

a chamber for receiving a sample of the liquid medium containing suspended particles;

a conduit for flow of the sample from the chamber;

means for drawing the sample through the conduit;

means for counting particles in the sample as it flows through the conduit; and metering means for accurately determining a sample volume equal to that in which the particles are to be counted, said metering means including a length of the conduit which is substantially electrically nonconductive, first and second electrodes spaced apart a predetermined distance along said conduit for being sequentially contacted by said sample as it passes therethrough, means responsive to an end of the sample passing the first contact to initiate the counting of particles, and means responsive to the same end of the sample passing the second contact to terminate the counting of particles whereby the number of particles counted represents those contained in a volume of sample equal to that present in the length of conduit between said electrodes, said means for initiating and terminating the counting of particles includes means for sensing a change in the conductivity of the path in said conduit length between the first and second electrodes, the means for initiating and terminating the counting of particles including a third electrode for being contacted by said sample, said third electrode being positioned along said conduit length and adjacent the second electrode, and means for sensing changes in the conductivity between said first and second electrodes and in the conductivity between said second and third electrodes whereby as an end of the sample passes said first, second and third electrodes the conductivity of the paths between said first and second and the second and third electrodes will sequentially change thereby to produce a first control signal to initiate counting and a second control signal to terminate counting, the first and second electrodes being positioned upstream from the third electrode with the trailing end first passing the first, second and third electrodes in that order whereby the first control signal is produced by the trailing end of the sample as it leaves the first electrode and the second control signal is produced as the sample's trailing end leaves the second electrode.

46. Apparatus for counting particles, such as blood cells, suspended in an electrically conductive liquid medium, comprising:

a chamber for receiving a sample of the liquid medium containing suspended particles;

a conduit for flow of the sample from the chamber;

a pair of electrodes positioned downstream from said inlet end of said conduit, each electrode being adapted for flow of sample therepast and for connection to a source of electrical energy whereby an electrical circuit path is completed between the electrodes through the sample when it is simultaneously flowing past both electrodes;

an electrically non-conductive membrane positioned between the electrodes and having an aperture therein sized to permit particles in the sample to pass therethrough, passage of a particle through the aperture momentarily affecting the conductivity of the electrical circuit path between the electrodes and producing a signal element of an electrical signal indicative of the number of particles to be counted;

means for drawing the sample through the conduit and the aperture;

a centering member bonded to each of the two opposite surfaces of said membrane and having a passage therethrough;

a first fitting having a passage communicating with the inlet end of said conduit and a second fitting communicating with the outlet end of said conduit, each fitting being relatively movable toward and away from each other; and means for clamping as a unitary assembly said bonded members and membrane between said fittings by relatively moving said fittings toward each other, said fittings and said centering members having mating configurations whereby the members when clamped between said fittings are positioned with the passages in said fittings and centering members all in communication with the aperture.

47. Apparatus as set forth in claim 46 wherein each of the fittings includes one of said electrodes.

48. Apparatus as set forth in claim 46 wherein said fittings constitute said electrodes and the axes of said passages in said fittings and said centering members are coaxially aligned with said aperture.

49. Apparatus as set forth in claim 48 wherein the centering members are annular in shape and the electrodes are cylindrical with the inner dimensions of the passages in the centering member being only slightly greater than the outer dimensions of the electrode whereby the unitary assembly of said bonded members and membrane is easily replaced when the fittings are moved apart and are self-centers upon the fittings being moved together when reclamping.

* * * * *